United States Patent
Ma et al.

(10) Patent No.: US 9,295,704 B2
(45) Date of Patent: Mar. 29, 2016

(54) COMPOSITION FOR PREVENTING OR TREATING ATOPIC DERMATITIS INCLUDING GALENICAL EXTRACT OR LACTOBACILLUS FERMENTATION THEREOF

(75) Inventors: Jin Yeul Ma, Daejeon (KR); Tae Ho Chung, Seoul (KR); Ga Young Im, Daejeon (KR); Dong Seon Kim, Daejeon (KR); Young Ran Um, Gyeongsangbuk-do (KR); Hyun Ae Eum, Gyeonggi-do (KR); Jae Hoon Lee, Daejeon (KR); Sung Up Choi, Daejeon (KR); Byoung Heon Cho, Gyeonggi-do (KR)

(73) Assignee: KOREA INSTITUTE OF ORIENTAL MEDICINE (KR)

( * ) Notice: Subject to any disclaimer, the term of this patent is extended or adjusted under 35 U.S.C. 154(b) by 0 days.

(21) Appl. No.: 13/825,839

(22) PCT Filed: Oct. 29, 2010

(86) PCT No.: PCT/KR2010/007523
§ 371 (c)(1),
(2), (4) Date: May 6, 2013

(87) PCT Pub. No.: WO2012/043920
PCT Pub. Date: Apr. 5, 2012

(65) Prior Publication Data
US 2013/0224181 A1    Aug. 29, 2013

(30) Foreign Application Priority Data
Sep. 28, 2010    (KR) .................. 10-2010-0093901

(51) Int. Cl.

| | | |
|---|---|---|
| A61K 35/00 | (2006.01) |
| A61K 33/04 | (2006.01) |
| A01N 59/02 | (2006.01) |
| A61K 36/258 | (2006.01) |
| A61K 8/97 | (2006.01) |
| A23L 1/30 | (2006.01) |
| A61K 36/23 | (2006.01) |
| A61K 36/232 | (2006.01) |
| A61K 36/25 | (2006.01) |
| A61K 36/28 | (2006.01) |
| A61K 36/296 | (2006.01) |
| A61K 36/355 | (2006.01) |
| A61K 36/484 | (2006.01) |
| A61K 36/489 | (2006.01) |
| A61K 36/634 | (2006.01) |
| A61K 36/725 | (2006.01) |
| A61K 36/78 | (2006.01) |
| A61K 36/808 | (2006.01) |
| A61Q 19/00 | (2006.01) |

(52) U.S. Cl.
CPC ............. *A61K 36/258* (2013.01); *A23L 1/3002* (2013.01); *A61K 8/97* (2013.01); *A61K 36/23* (2013.01); *A61K 36/232* (2013.01); *A61K 36/25* (2013.01); *A61K 36/28* (2013.01); *A61K 36/296* (2013.01); *A61K 36/355* (2013.01); *A61K 36/484* (2013.01); *A61K 36/489* (2013.01); *A61K 36/634* (2013.01); *A61K 36/725* (2013.01); *A61K 36/78* (2013.01); *A61K 36/808* (2013.01); *A61Q 19/00* (2013.01); *A61K 2800/85* (2013.01)

(58) Field of Classification Search
None
See application file for complete search history.

(56) References Cited

U.S. PATENT DOCUMENTS

| 2007/0166405 A1* | 7/2007 | Song et al. ................... 424/725 |
| 2009/0169531 A1* | 7/2009 | Lacoste et al. ............. 424/93.45 |
| 2009/0170787 A1 | 7/2009 | Park |
| 2011/0052731 A1* | 3/2011 | Park et al. .................... 424/728 |
| 2012/0045422 A1* | 2/2012 | Crane et al. ................ 424/93.45 |

FOREIGN PATENT DOCUMENTS

| CN | 1736439 A | 2/2006 |
| CN | 101804166 A | 8/2010 |
| CN | 101810799 A | 8/2010 |
| JP | 11-158053 A | 6/1999 |

(Continued)

OTHER PUBLICATIONS

Joo et al., Phtother., 23:913-919 (2009).*

(Continued)

*Primary Examiner* — Blaine Lankford
*Assistant Examiner* — Thomas J Visone
(74) *Attorney, Agent, or Firm* — Merchant & Gould P.C.

(57) ABSTRACT

The present invention relates to a pharmaceutical composition and health supplement for preventing or treating atopic dermatitis, the composition and supplement having as active ingredients extract of a galenical mixture including *sophora* root, licorice, lonicer aflower, Korean *angelica* root, Korean *aralia* root, *saussurea* root, *seselos radix*, *zizyphus spinosi*, *Houttuynia cordata*, *forsythia* fruit, lappa fruit, *Epimedium koreanum* Nakai, *ginseng*, lithospermum, oleoresin, *cnidium*, *scorophulariae radix*, and *reynoutria*, or *lactobacillus* fermentation of the galenical extract prepared by inoculating *lactobacillus* to the galenical extract and fermenting same. The galenical extract or the galenical extract fermentation of the present invention achieves reduced scratching, decreases clinical features of atopic symptoms such as erythema, itchiness and dry skin, edema and hematoma, erosion, and lichenification, and reduces IgE concentration in blood, which is related to exogenous atopic dermatitis, in laboratory animal models of atopic dermatitis, and is thereby, useful for preventing or treating atopic dermatitis.

13 Claims, 3 Drawing Sheets

(56) References Cited

FOREIGN PATENT DOCUMENTS

| | | | |
|---|---|---|---|
| JP | 2000-154113 A | 6/2000 | |
| JP | 2002-053428 A | 2/2002 | |
| JP | 2004-083449 A | 3/2004 | |
| JP | 2004-155664 A | 6/2004 | |
| JP | 2005-089403 A | 4/2005 | |
| JP | 2006-008566 A | 1/2006 | |
| JP | 2006-347907 A | 12/2006 | |
| JP | 2007-186457 A | 7/2007 | |
| JP | 2009-517461 A | 4/2009 | |
| KR | 10-2004-0000046 | 1/2004 | |
| KR | 10-2004-0000046 A | 1/2004 | |
| KR | 10-2006-0092373 A | 8/2006 | |
| KR | 10-2006-0118809 A | 11/2006 | |
| KR | 10-2007-0079497 | 8/2007 | |
| KR | 10-2007-0079497 A | 8/2007 | |
| KR | 10-2007-0096163 A | 10/2007 | |
| KR | 100832332 * | 5/2008 | A61K 31/22 |
| KR | 10-0855456 B1 | 9/2008 | |
| KR | 10-2008-0099570 A | 11/2008 | |
| KR | 10-2009-0009480 A | 1/2009 | |
| KR | 10-2009-0023236 A | 3/2009 | |
| KR | 10-2009-0075950 | 7/2009 | |
| KR | 10-2009-0075950 A | 7/2009 | |
| KR | 10-2009-0125726 | 12/2009 | |
| KR | 10-2010-0093151 | 8/2010 | |
| WO | WO 2006/123887 A1 | 11/2006 | |
| WO | WO 2007/064085 A1 | 6/2007 | |

OTHER PUBLICATIONS

Lee et al., Abstract (2004).*
Kim et al. Biosci. Biotechnol Biochem., 71(12):2886-2892 (2007).*
Lee et al., Arch. Pharm. Res., 26(5):367-374 (2003).*
Grassberger et al., "A novel anti-inflammatory drug, SDZ ASM 981, for the treatment of skin diseases: in vitro pharmacology," *British Journal of Dermatology*, 141:264-73 (1999).
Wasik et al., "Effects of FK-506 and cyclosporine on human T and B lymphoproliferative responses," *Immunopharmacology*, 20:57-61 (1990).
International Search Report for International Application No. PCT/KR2010/007523 mailed Nov. 10, 2011.
Office Action from Japanese Patent Application No. 2013-530081 (mailed Feb. 24, 2015).
Extended European Search Report for European Patent Application No. 10857921.0 (mailed Feb. 10, 2014).
Shim et al., "Inhibitory Effects of Fermented Nutraceuticals on NO Production and T Cell Proliferation in Juvenile Atopic Dermatitis", *Journal of Physiological Anthropology*, 26(2): p. 225-227 (Mar. 2007).
Yamaguchi-Miyamoto et al., "Antipruritic effects of Sophora flavescens on acute and chronic itch-related responses in mice", *Biological & Pharmaceutical Bulletin*, 26(5): p. 722-724 (May 2003).
Joo et al., "Therapeutic Advantages of Medicinal Herbs fermented with *Lactobacillus plantarum*, in Topical Application and its Activities on Atopic Dermatitis", *Phytotherapy Research*, 23(7): p. 913-919 (Jul. 2009).
Tohda et al., "Inhibitory Effect of Byakko-ka-ninjin-to on Itch in a Mouse Model of Atopic Dermatitis",*Phytotherapy Research*, 14(3): p. 192-194 (May 2000).
Kim et al., "Anti-inflammatory effects of YeongyoSeungma-tang", *Journal of Ethnopharmacology*, 126(3): p. 377-381 (Dec. 2009).
Sohn et al., "Screening of Anti-Acne Activity of Natural Products against *Propionibacterium acnes*", *Kor. J. Micorbiol. Biotechnol.*, 34(3): p. 265-272 (Sep. 2006).
Office Action from Chinese Patent Application No. 201080069308.1 (mailed Mar. 18, 2014).
Office Action from Japanese Patent Application No. 2013-530081 (mailed Jun. 3, 2014).
Guo et al., "The Study of Chinese Herbs in the Treatment of Atopic Dermatitis", *Henan Traditional Chinese Medicine*, 27(4): p. 83-85 (2007).
Zhang et al., "Zymotic Technique and The Research of TCM", *Journal of Guangdong Industry Technical College*, 4(1):p. 34-37 (2005).
Notice of Allowance for corresponding Japanese Patent Application No. 2013-530081 (mailed Jan. 5, 2016).
Patent Gazette for corresponding Chinese Patent Publication No. 103228287 B (Dec. 2, 2015).

* cited by examiner

COMPOSITION FOR PREVENTING OR TREATING ATOPIC DERMATITIS INCLUDING GALENICAL EXTRACT OR LACTOBACILLUS FERMENTATION THEREOF

This application is a National Stage Application under 35 U.S.C. §371 of PCT/KR2010/007523, filed 29 Oct. 2010, which claims the benefit of priority to Korean Patent Application No. 10-2010-0093901, filed 28 Sep. 2010, the disclosures of all of which are hereby incorporated by reference in their entireties. The International Application was published in Korean on Apr. 5, 2012 as WO 2012/043920. To the extent appropriate, a claim of priority is made to each of the above disclosed applications.

FIELD OF THE INVENTION

The present invention relates to a composition for the prevention or treatment of atopic dermatitis, more precisely a composition that can be effectively used for the prevention and/or treatment of atopic dermatitis comprising the extract of herb mixture containing *Sophora flavescens*, Licorice (*Glycyrrhiza uralensis*), *Lonicera jabonica*, *Angelica gigas*, *Aralia continentalis*, *Saussurea lappa*, *Bangpoong* (*Saposhnikovia divaricata*), *Zizyphus jujuba*, *Houttuynia cordata*, *Forsythia koreana*, *Arctii Fructus*, *Epimedium koreanum*, *Ginseng*, *Lithospermi Radix*, *Sanguisorbae officinalis*, *Cnidium officinale*, *Scrophularia buergeriana*, and *Reynoutria elliptica* or the lactic acid bacteria fermented solution thereof as an active ingredient.

DESCRIPTION OF THE RELATED ART

Atopy is the skin disease first described by Cocca in 1925, that is a congenital allergic reaction against foods and inhalant substances causing dermatitis, asthma, or hay fever. Atopic disease includes not only atopic dermatitis, but also asthma, allergic rhinitis and allergic conjunctivitis. Atopy accompanies allergic reaction. Atopic dermatitis showing characteristic morphology and distribution of skin lesion is chronic or recurrent dermatitis that is a skin disease very familiar in those who have a genetic predisposition to atopic disease, meaning who has a family history of atopic disease. In general, atopic dermatitis starts in infancy and in early childhood, particularly around two months of age. Approximately 50% of atopic dermatitis starts before two years of age and most atopic dermatitis starts before 5 years of age. It is very rare that atopic dermatitis develops its first symptom in adulthood. In most cases, symptoms of atopic dermatitis are alleviated or gone as patients grow. More than half of toddler patients are relieved from the symptoms before being two years old. 0.7% of people and 35% of children under the age of 5 are atopic dermatitis patients and the number is increasing every year because of environmental factors.

Atopic dermatitis starts with lupus erythematosus accompanying racking itchiness and scales. When it gets worse, the symptoms turn to acute symptoms carrying blisters, serous effusions and crusts. The most characteristic symptom of atopic dermatitis is severe pruritus so that patients cannot help scratching to bleeding. The cycle of itching and scratching and itching again repeats and makes the symptom worse, resulting in lichenification characterized by thickness and wrinkles on skin. Most of the clinical features are resulted from scratching or scrubbing. Such pruritus gets worse in the night, causing sleep disturbance. Recently, incidence of atopic dermatitis is increasing world-widly, which is presumably attributed to air pollution, increased chances of exposing on antigens due to changes in residential environment, decrease of breast-feeding, and decrease of childhood infectious disease, etc. According to the national epidemiological survey performed by KAPARD (The Korean Academy of Pediatric Allergy and Respiratory Disease) in 1995, 12-24% of elementary school students and 6-8% of middle school students have been diagnosed with atopic dermatitis. In 2000, 24.9% of elementary school students and 12.8% of middle school students have been diagnosed with atopic dermatitis and even in adult incidence of atopic dermatitis increases in Korea.

The exact pathophysiology of atopic dermatitis has not been clearly understood, yet. It has only been presumed that the said disease is attributed to genetic factors along with immunological or noneimmunological mechanisms. Extrinsic atopic dermatitis is developed by the IgE related immunomechanism. It has also been reported that T-cell mediated primary immune response is more likely involved than secondary immune response against a specific allergen. It has also been confirmed that the increase of IgE is related to the dysfunction of cell mediated immunity in atopic dermatitis patients. Accordingly, it has been issued that primary immune response, in addition to secondary immune response, is also involved in atopic dermatitis development (Kiyoung Lee, Current Treatment of Allergy, HangukEuihakSa, Seoul, 2001, pp. 2352).

Therapeutic agents for atopic dermatitis have been developed considering the known causes, mechanisms, and symptoms of atopic dermatitis up to date. As a result, natural or synthetic immune inhibitors, anti-histamine agents, and steroids, etc have been developed. For example, Cyclosporin A, FK506 (Tacrolimus; Wasik, et al., Immunopharmacology 20:57-61, 1990), and SDZ ASM981 (Pimecrolimus; Grassberger, et al., Br. J. Dermatology 141:264-273, 1999) hold the limelight as immune inhibitors. However, the conventional treating agents for atopic dermatitis, steroids and anti-histamine agents, can only relieve symptoms temporarily. When topical or oral steroids are administered for a long term, the skin of a patient wears thin and osteoporosis is induced. In particular among child patients, such long term administration results in the inhibition of growth and thereby local and systemic side effect might be induced. If it gets worse, systemic symptoms can be induced by the hormone and if the administration is stopped, the symptoms get worse, indicating resistance against steroids. Therefore, it is requested to develop a novel anti-atopic agent using a natural substance which is effective in treatment but has less side effects.

The present inventors searched herb extracts that can be effectively used for the improvement of atopic dermatitis. Particularly, the present inventors prepared an herb extract from the herb mixture composed of *Sophora flavescens*, Licorice (*Glycyrrhiza uralensis*), *Lonicera jabonica*, *Angelica gigas*, *Aralia continentalis*, *Saussurea lappa*, *Bangpoong* (*Saposhnikovia divaricata*), *Zizyphus jujuba*, *Houttuynia cordata*, *Forsythia koreana*, *Arctii Fructus*, *Epimedium koreanum*, *Ginseng*, *Lithospermi Radix*, *Sanguisorbae officinalis*, *Cnidium officinale*, *Scrophularia buergeriana* and *Reynoutria elliptica*, and a lactic acid fermented solution thereof. And, the present inventors confirmed that the herb extract or the lactic acid fermented solution thereof was effective in the prevention or treatment of atopic dermatitis, which had never been reported before, leading to the completion of the present invention.

SUMMARY OF THE INVENTION

It is an object of the present invention to provide a composition for the prevention or treatment of atopic dermatitis comprising an herb extract or a lactic acid bacteria fermented solution thereof as an active ingredient.

To achieve the above object, the present invention provides an herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or a lactic acid bacteria fermented solution thereof.

The present invention also provides a pharmaceutical composition for the prevention or treatment of atopic dermatitis comprising the herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

The present invention further provides a health food for the prevention and treatment of atopic dermatitis comprising the herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

In addition, the present invention provides a cosmetic composition for the prevention or treatment of atopic dermatitis comprising the herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

Advantageous Effect

As explained hereinbefore, the herb extract or the fermented herb extract of the present invention had the effect of relieving the symptoms of atopic dermatitis. Particularly, the frequency of scratching was decreased and other clinical symptoms of atopic dermatitis such as erythema, pruritus & dry skin, edema & excoriation, erosion, and lichenification were all reduced. In addition, the level of blood IgE involved in extrinsic atopic dermatitis was reduced by the administration of the herb extract or the fermented herb extract of the present invention. Therefore, the herb extract or the fermented herb extract of the present invention can be effectively used for the prevention and/or treatment of atopic dermatitis.

BRIEF DESCRIPTION OF THE DRAWINGS

The application of the preferred embodiments of the present invention is best understood with reference to the accompanying drawings, wherein:

FIG. 3 is a graph illustrating that the test animal induced with atopic dermatitis was administered with the herb extract or the fermented herb extract of the present invention, followed by scoring for each symptom such as erythema, pruritus & dry skin, edema & excoriation, erosion, and lichenification on day 1, day 3, day 7, and day 14. Each score for symptom was as follow: 0 (symptom was not shown), 1 (weak symptom), 2 (usual symptom), and 3 (severe symptom). Scores for the above 5 symptoms were summed. AD: induced with atopic dermatitis or not (+: induced with atopic dermatitis, −: not induced with atopic dermatitis), KIOM-MA: administered with the herb extract/fermented herb extract or not (+: administered, −: not administered), C: the herb extract of the present invention, 128: the fermented herb extract of the present invention, PC: positive control (Dexa.1; dexamethasone 1 mg/kg).

DESCRIPTION OF THE PREFERRED EMBODIMENTS

Hereinafter, the present invention is described in detail.

The present invention provides an herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or a lactic acid bacteria fermented solution thereof.

The said herb extract is preferably extracted from the herb mixture composed of 10 weight parts of *Sophora flavescens*, 2-8 weight parts of Licorice (*Glycyrrhiza uralensis*), 2-8 weight parts of *Lonicera jabonica*, 2-8 weight parts of *Angelica gigas*, 2-8 weight parts of *Aralia continentalis*, 2-8 weight parts of *Saussurea lappa*, 2-8 weight parts of Bangpoong (*Saposhnikovia divaricata*), 2-8 weight parts of *Zizyphus jujuba*, 5-15 weight parts of *Houttuynia cordata*, 2-8 weight parts of *Forsythia koreana*, 5-15 weight parts of *Arctii*

*Fructus*, 2-8 weight parts of *Epimedium koreanum*, 5-15 weight parts of *Ginseng*, 2-8 weight parts of *Lithospermi Radix*, 2-8 weight parts of *Sanguisorbae officinalis*, 2-8 weight parts of *Cnidium officinale*, 5-15 weight parts of *Scrophularia buergeriana*, and 2-8 weight parts of *Reynoutria elliptica*. As an extraction solvent, water is generally used, but if necessary other organic solvents can be used. The usable organic solvent is exemplified by $C_1$-$C_4$ lower alcohols, aceton or its aqueous solution, but not always limited thereto. In this invention, the said "herb extract" can be extracted from the herb mixture above not only by using water as a solvent but also by using other organic solvents.

In a preferred embodiment of the present invention, to prepare the lactic acid fermented solution from the herb extract (can be referred as "fermented herb" or "fermented herb extract" hereinafter), water was added to the said herb mixture at the volume of 2-5 times the mixture volume, followed by hot-water extraction at 70-130° C. obtain a water extract. The obtained water extract was cooled down, to which lactic acid bacteria were inoculated by 0.5-5 weight %, preferably by 1 weight %. Then, the fermented herb extract of the present invention was prepared by fermenting the water extract at 20-40° C., preferably at 37° C. for 24-52 hours, preferably for 48 hours. In the case of preparing the fermented herb extract by using other organic solvents instead of water, the herb extract needed to be dried first and then diluted in water, to which lactic acid bacteria were inoculated before fermentation.

In this invention, any isolated lactic acid bacterial strain or commercial lactic acid bacterial strain can be used as the lactic acid bacteria. Particularly, *Lactobacillus* sp., *Bifidobacterium* sp., *Streptococcus* sp., *Leuconostoc* sp., *Pediococcus* sp., or *Lactococcus* sp. Strain can be used without limitation, but among them *Lactobacillus* sp. strain is more preferred. In a preferred embodiment of the present invention, the fermented herb extract was prepared by using a variety of lactic acid bacterial strains such as *Lactobacillus acidophilus, L. casei, L. plantarum, L. fermentum, L. bulgaricus, L. delbruekii* subsp. *lactis, L. gasseri,* and *Bifidobacterium breve* (see Example 2). However, the applicable lactic acid bacterial strain is not limited thereto, and the lactic acid bacteria culture medium can be selected from the group consisting of MRS (Man-Rogosa-Sharpe), lactose, M17, and APT (Asparagline Enrichment Broth), but not always limited thereto, either.

The present invention also provides a pharmaceutical composition for the prevention or treatment of atopic dermatitis comprising the herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

In this invention, "atopic dermatitis" includes all the disease classified as atopic dermatitis in this field regardless of cause, either induced directly or indirectly. Atopic dermatitis is generally divided into infancy atopic dermatitis, childhood atopic dermatitis, adult atopic dermatitis, and pregnancy atopic dermatitis, according to the time or subject of onset. In this invention, atopic dermatitis includes all the above types of atopic dermatitis.

The herb extract or the fermented herb extract of the present invention can be administered orally or parenterally and be used in general forms of pharmaceutical formulation. That is, herb extract or the fermented herb extract of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the said betaine with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The dosage units can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose.

The effective dosage of the herb extract of the fermented herb extract of the present invention for human can be determined according to absorptiveness of the active ingredient, inactivation rate, excretion rate, age, gender, health condition and severity of a disease, etc. In general, the daily dose for adult is 10-300 mg/kg, and preferably 20-10 mg/kg, which can be administered 1-6 times a day.

In a preferred embodiment of the present invention, a test animal induced with atopic dermatitis was administered with the herb extract or the fermented herb extract of the present invention. The frequency of scratching was reduced the extract dose-dependently. In particular, when the fermented herb extract was administered, the frequency of scratching was significantly reduced (see FIG. 2).

In another preferred embodiment of the present invention, atopic dermatitis was clinically evaluated by summing up the scores for each erythema, pruritus & dry skin, edema & excoriation, erosion, and lichenification made by visual evaluation. The scores indicating severe skin trouble were decreased when the herb extract or its fermented solution of the present invention was administered. In particular, the scores were significantly decreased by the administration of the fermented herb extract of the present invention (see FIG. 3).

In another preferred embodiment of the present invention, any change in Th1/Th2 immune response by environmental stress was investigated. To do so, blood sample was taken from the mouse at different time points, from which serum was isolated. IgE in the serum was measured by using ELISA kit. As a result, IgE level in the serum was decreased by the herb extract and its fermented solution of the present invention dose-dependently (see FIG. 4).

The present invention also provides a health food for the prevention and alleviation of atopic dermatitis comprising the herb extract extracted from the herb mixture composed of *Sophora flavescens*, Licorice (*Glycyrrhiza uralensis*),

*Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

The herb extract or the lactic acid bacteria fermented herb extract of the present invention can be added to health food to improve the symptoms of atopic dermatitis. In that case, the herb extract or the fermented herb extract can be added as it is or as mixed with other food components according to the conventional method. The mixing ratio of active ingredients can be regulated according to the purpose of use (prevention, health enhancement or treatment). In general, to produce health food or beverages, the herb extract or the fermented herb extract is added preferably by up to 30 weight % and more preferably by up to 10 weight %. However, if long term administration is required for health and hygiene or regulating health condition, the content can be lower than the above but higher content can be accepted as well since the herb extract or the fermented herb extract of the present invention has been proved to be very safe.

The food herein is not limited. For example, the herb extract or the fermented herb extract of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc., like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 gin 100 ml of the composition.

In addition to the ingredients mentioned above, the herb extract or the fermented herb extract of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The herb extract or the fermented herb extract of the present invention can also include fruit flesh addable to natural fruit juice, fruit beverages and vegetable beverages. All the mentioned ingredients can be added singly or together. The mixing ratio of those ingredients does not matter in fact, but in general, each can be added by 0.01-0.1 weight part per 100 weight part of the herb extract or the fermented herb extract of the present invention.

In addition, the present invention provides a cosmetic composition for the prevention or improvement of atopic dermatitis comprising the herb extract extracted from the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana* and *Reynoutria elliptica*, or the lactic acid fermented solution thereof as an active ingredient.

The form of the cosmetic composition of the present invention is not limited but is preferably an external preparation for skin. The preferable example of the external preparation for skin is skin, lotion, massage cream, nourishing cream, pack, gel or adhesive type cosmetic composition. A transdermal preparation such as lotion, ointment, gel, cream, patch or spray is also preferable formulation. The composition for external preparation in whatever forms can include any other ingredients in addition to the said essential active ingredient, and these ingredients can be selected by those in the art considering the purpose or the formulation of the preparation.

When the cosmetic composition of the present invention is applied in cosmetics, skin scientifically acceptable medium or base can be included. The proper formulation can be exemplified by solution, gel, solid or dough anhydride, emulsion prepared by dispersing oil phase on water phase, suspension, microemulsion, microcapsule, microgranule, ionic (liposome) and/or non-ionic vesicle, cream, skin, lotion powder, spray, and conceal stick. In addition, the cosmetic composition can be formulated as an aerosol composition containing foam or compressed propellant. In addition, it can be formulated as a supplement for local or systemic application generally used in the field of skin science by containing skin scientifically acceptable medium or base.

The cosmetic composition of the present invention can additionally include a supplement generally used in the field of cosmetology such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamine, blocker, moisturing agent, essential oil, dye, pigment, hydrophilic or hydrophobic activator, lipid vesicle or other components generally used for the preparation of cosmetics. The amount of the above supplement can be determined as generally accepted in the field of cosmetology.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of Herb Extract

The herb extract of the present invention is an Oriental pharmaceutical preparation prepared by extracting the herb mixture composed of *Sophora flavescens*, Licorice (*Glycyrrhiza uralensis*), *Lonicera jabonica, Angelica gigas, Aralia continentalis, Saussurea lappa*, Bangpoong (*Saposhnikovia divaricata*), *Zizyphus jujuba, Houttuynia cordata, Forsythia koreana, Arctii Fructus, Epimedium koreanum, Ginseng, Lithospermi Radix, Sanguisorbae officinalis, Cnidium officinale, Scrophularia buergeriana*, and *Reynoutria elliptica*. Particularly, the herb mixture was prepared with 160 g of *Sophora flavescens*, 80 g of Licorice (*Glycyrrhiza uralensis*), 80 g of *Lonicera jabonica*, 80 g of *Angelica gigas*, 80 g of *Aralia continentalis*, 80 g of *Saussurea lappa*, 80 g of Bangpoong (*Saposhnikovia divaricata*), 80 g of *Zizyphus jujuba*, 160 g of *Houttuynia cordata*, 80 g of *Forsythia koreana*, 160 g of *Arctii Fructus*, 80 g of *Epimedium koreanum*, 160 g of *Ginseng*, 80 g of *Lithospermi Radix*, 80 g of *Sanguisorbae officinalis*, 80 g of *Cnidium officinale*, 160 g of *Scrophularia buergeriana*, and 80 g of *Reynoutria elliptica*. The herb mixture in the total volume of 1,840 g was mixed with 18.4 l of distilled water (10 times the volume of the mixture), which stood for 1 hour for immersion, followed by extraction using a high-speed vacuum extractor (cosmos-600, Kyungseo Machine, korea) at 115° C. for 3 hours. The obtained extract was filtered with standard testing sieve (Aperture 500 μm and 150 μm). As a result, the herb extract of the present invention was prepared.

Example 2

Preparation of Lactic Acid Bacteria Fermented Herb Extract

<2-1> Seed Culture of Lactic Acid Bacteria

Lactic acid bacteria used for the preparation of the lactic acid fermented herb extract of the present invention are as follows: *Lactobacillus rhamnosus* (KFRI #128), *L. casei* (KFRI #127), *L. plantarum* (KFRI #144, KFRI #402), *L. fermentum* (KFRI #164), *L. bulgaricus* (KFRI #344), *L. delbruekii* subsp. *Lactis* (KFRI #442), *L. gasseri* (KFRI #658, KCTC 3163), and *Bifidobacterium breve* (KFRI #744). The said strains were sub-cultured on slant medium and in liquid medium, being prepared for the experiments. Particularly, lactic acid bacteria were inoculated on slant medium, followed by culture at 37° C., for 24 hours. Once colonies were formed, oxygen was blocked by using paraffin film. The slant medium was then stored in a refrigerator. To prevent the strain from losing its activity or from being contaminated with other bacteria, the colonies were inoculated on fresh slant agar medium every 2-3 weeks. Then, the colonies were inoculated in liquid medium, followed by culture at 37° C., for 24 hours. MRS medium (10 g/l Peptone, 10 g/l Beef extract, 5 g/l Yeast extract, 20 g/l Glucose, 1 ml/l Tween 80, 2 g/l $K_2HPO_4$, 5 g/l Sodium acetate, 2 g/l Triammonium citrate, 0.2 g/l $MgSO_4 \cdot 7H_2O$, 0.2 g/l $MnSO_4 \cdot 4H_2O$, pH 6.2-6.6) was used for the seed culture.

<2-2> Fermentation of Herb Extract Using Lactic Acid Bacteria pH of the herb extract prepared in Example 1 was adjusted to 8.0 by using 1 M NaOH, and the extract was autoclaved (121° C., 1.5 atm, 15 min), which was then cooled down to room temperature. Before fermentation, pH of the control was lowered to 6.3 from 8.0. This was because some of dietary fibers included in the herb extract were decomposed and turned to organic acid under the high-temperature high-pressure condition (121° C., 1.5 atm, 15 min). The said lactic acid bacteria ($1-5\times10^8$ CFU/ml) were added to the herb extract at the volume of 1% (v/v), followed by aeration culture at 37° C. for 48 hours, leading to liquid fermentation. The culture solution was then filtered with standard testing sieve. As a result, the lactic acid bacteria fermented herb extract of the present invention was prepared. The changes of dry weight and pH of the lactic acid bacteria fermented herb extract were as shown in Table 1.

TABLE 1

| | pH | Dry weight (%) |
|---|---|---|
| Control | 6.19 ± 0.00 | 2.97 ± 0.02 |
| KFRI 127 | 4.42 ± 0.01 | 3.02 ± 0.01 |
| KFRI 128 | 4.00 ± 0.01 | 2.97 ± 0.03 |

TABLE 1-continued

| | pH | Dry weight (%) |
|---|---|---|
| KFRI 144 | 4.26 ± 0.00 | 2.97 ± 0.02 |
| KFRI 164 | 4.52 ± 0.00 | 3.04 ± 0.00 |
| KFRI 344 | 4.36 ± 0.01 | 3.06 ± 0.01 |
| KFRI 402 | 4.34 ± 0.01 | 3.02 ± 0.02 |
| KFRI 442 | 4.03 ± 0.01 | 3.02 ± 0.00 |
| KFRI 658 | 4.65 ± 0.01 | 2.88 ± 0.04 |
| KFRI 744 | 3.84 ± 0.01 | 2.88 ± 0.00 |
| KCTC 3163 | 4.25 ± 0.01 | 3.00 ± 0.02 |

From the above results, it was confirmed that pH of the herb extract was lowered to 4.0 by the lactic acid bacteria fermentation, indicating active acid producing capability therein. The lactic acid bacteria fermented herb extract of the present invention was freeze-dried and stored at 4° C. until use.

<2-3> Analysis of Lactic Acid Bacteria Fermented Herb Extract

Residue in the lactic acid bacteria fermented herb extract prepared above was eliminated by centrifugation, which was then filtered with 0.45 μm filter. HPLC was performed under the conditions shown in Table 2.

TABLE 2

| Column | Reversed Phase Column ($C_{18}$, 250 × 4.6 mm, 5 μm) |
|---|---|
| Detector | UV 254 nm |
| Solvent A | 2% acetic acid |
| B | Acetonitrile |
| Running Time | 65 min |
| Loading Volume | 20 μl |
| Flow Rate | 1.0 ml/min |

| Density Gradient Table | |
|---|---|
| Time | A/B |
| 0 | 80/20 |
| 5 | 80/20 |
| 50 | 20/80 |
| 55 | 80/20 |
| 65 | 80/20 |

Figure 1:
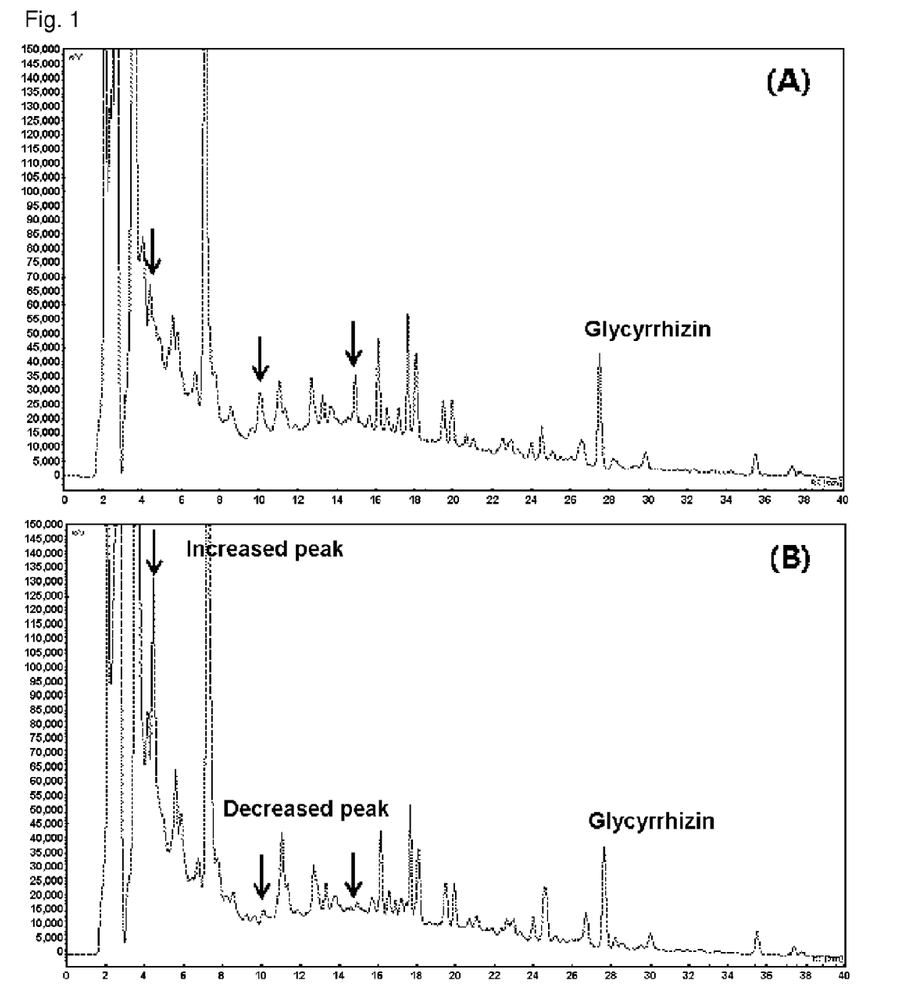
FIG. 1 is a diagram showing the chromatograms of the herb extract (A) and the lactic acid bacteria fermented herb extract (B) of the present invention.

As a result, in the case of the herb extract fermented by *Lactobacillus rhamnosus* (KFRI #128), the peak at the time point of 4.5 min. was 4.3 fold increased, compared with that of the herb extract not fermented. In the meantime, the peaks at the time points of 10.1 min. and 14.9 min. were decreased with fermentation (68% and 79% respectively). Glycyrrhizin (27.5 min.), one of the important index materials for the herb extract of the present invention, was detected both before and after the fermentation with lactic acid bacteria (FIG. 1).

Experimental Example 1

Scratching Behavior Test

In this example, the following experiments were performed according to the "Guideline for efficacy test of herbal preparations—atopic dermatitis" (guideline administration No. 1-019-2010-0000 (0)) provided by Biopharmaceuticals and Herbal Medicine Bureau, Korea Food & Drug Administration. Test animals were raised in the cage, where the temperature was maintained at 23±3° C. with the humidity of 50±5% and the day/night cycle was regulated at 12 hours intervals. The basic diet for the test animal was prepared according to the guideline provided by American Institute Nutrition (1970). The test material was mixed with liquid solvent (drinking water). The preparation was performed according to the 'Composition and preparation of test material (NITR/SOP/TSB/002_02)' described in the standard operating procedure provided by National Institute of Food and Drug Safety Evaluation, Korea. To make each dose group has homogeneity, each animal was allotted to each experimental group according to the 'Rodents, random distribution of cage and rack (NITR/SOP/GTX/002_02)' described in the standard operating procedure provided by National Institute of Food and Drug Safety Evaluation, Korea. To evaluate statistic significance of the test results, each group was organized with 5-7 test animals, and significance was confirmed by using Wilcoxon rank-sum test (Mann-Whitney test) with the changes of numerical number and error of both test and control groups. Statistics program used herein was SAS. Statistics program used herein was SAS.

For the scratching behavior test, the female BALB/c mouse at 7 weeks was administered with ovalbumin (OVA, 20 μg) and aluminum hydroxide (2.25 mg) hyperdemically on day 0 and day 14 to induce atopic dermatitis. The herb extract and the fermented herb extract prepared in Example 1 and Example 2 were administered to the test animal once a day at the concentration of 50 or 100 mg/kg. Scratching frequency was measured 30 minutes before and after the administration for 15 minutes. At this time, the herb extract fermented by *Lactobacillus rhamnosus* (KFRI #128) was used as the fermented herb extract.

Figure 2:
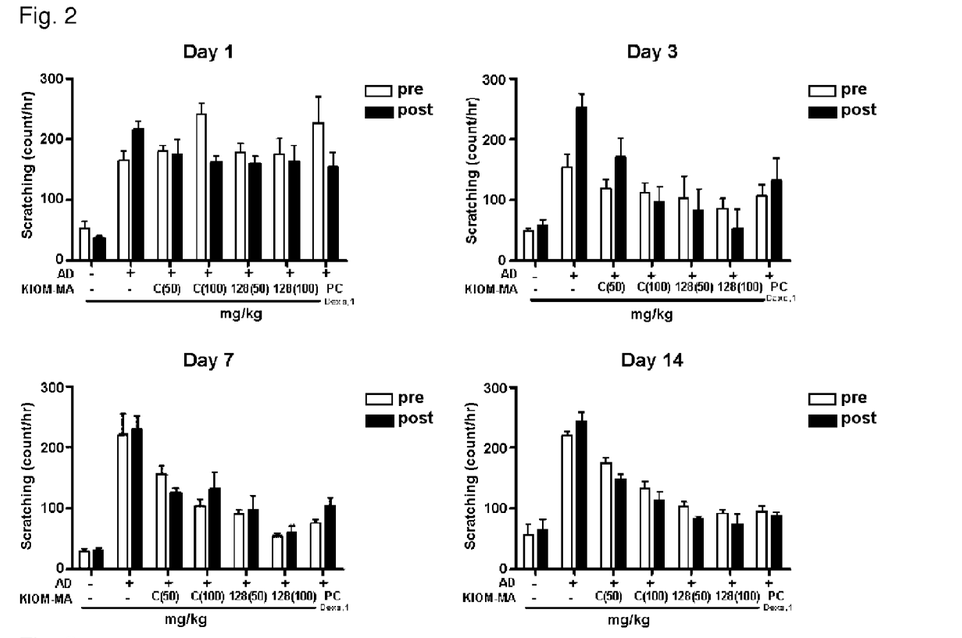
FIG. 2 is a graph illustrating the frequency of scratching observed on day 1, day 3, day 7, and day 14 after the administration of the herb extract or the lactic acid bacteria fermented herb extract of the present invention to the test animal induced with atopic dermatitis. AD: induced with atopic dermatitis or not (+: induced with atopic dermatitis, −: not induced with atopic dermatitis), KIOM-MA: administered with the herb extract/fermented herb extract or not (+: administered, −: not administered), C: the herb extract of the present invention, 128: the fermented herb extract of the present invention, PC: positive control (Dexa.1; dexamethasone 1 mg/kg).

As a result, the frequency of scratching was reduced by the administration of the herb extract or the fermented herb extract dose-dependently. In particular, in the group treated with the fermented herb extract at the dose of 100 mg/kg, the frequency of scratching was significantly reduced from the third day of the administration, compared with not only that in the negative control but also that in the positive control. Even after 14 days from the administration, significant difference was observed (p<0.01) (FIG. 2).

Experimental Example 2

Sensory Evaluation

This evaluation method is the clinical visual evaluation method which has been generally used to evaluate atopic dermatitis. According to this method, the severity of atopic dermatitis was presented with the total score obtained by summing the scores for 5 evaluation items. The evaluation items were erythema, pruritus & dry skin, edema & excoriation, erosion, and lichenification. For each item, points were given as follows: 0 (symptom was not shown), 1 (weak symptom), 2 (usual symptom), and 3 (severe symptom). After summing the points obtained from the above 5 times, evaluation point was given from 0 (no sign of symptom) to 15 points (symptoms are severe in all the items).

Figure 3:
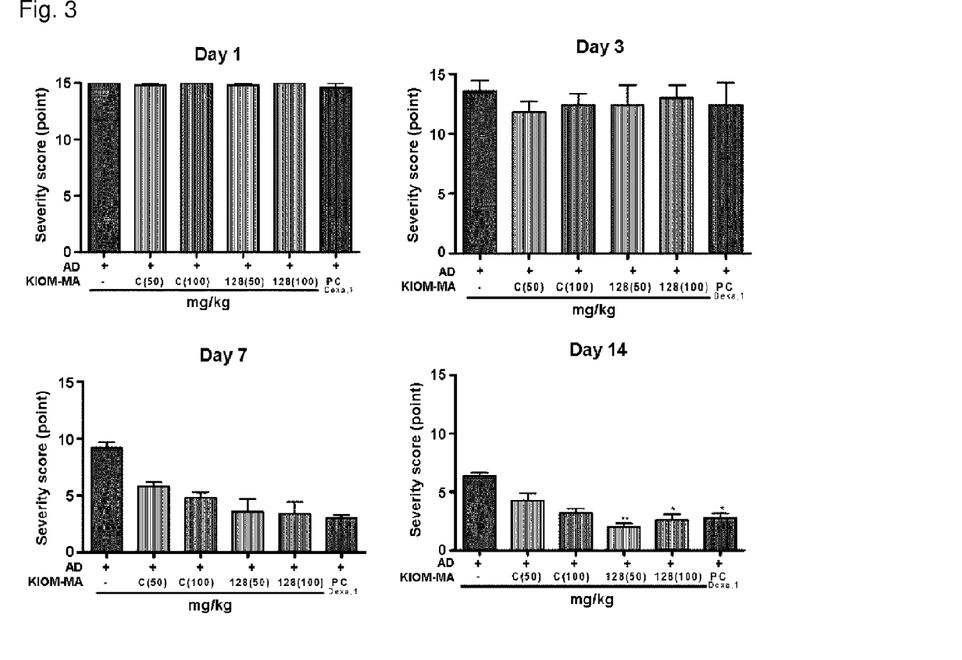

As a result, when the herb extract and the fermented herb extract of the present invention were administered, skin seriousness scores were reduced. In particular, when the fermented herb extract of the present invention was administered, skin seriousness scores were significantly reduced, compared with the negative control (p<0.01) (FIG. 3).

Experimental Example 3

Effect on Blood IgE

It was expected that blood IgE level would be raised over the week in the mouse induced with atopic dermatitis by environmental stimuli, compared with the control mouse. To investigate the change of Th1/Th2 immune response by environmental stress, blood was drawn from the mouse, from which serum was isolated. IgE level was measured by using ELISA kit to evaluate whether blood IgE level was increased or decreased by the test material.

Figure 4:
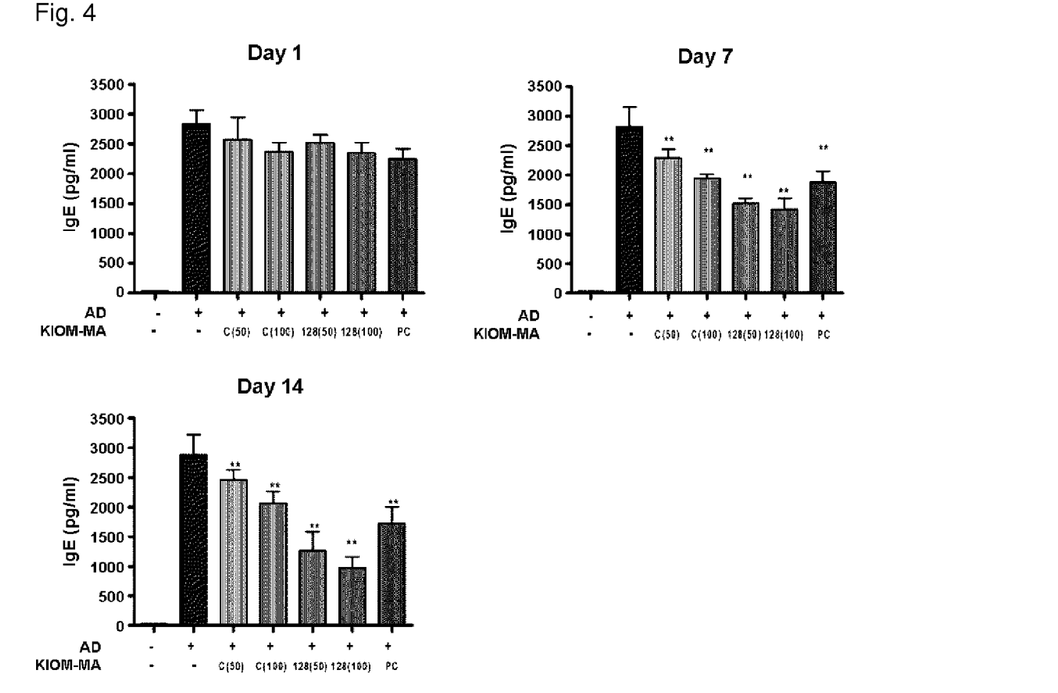
FIG. 4 is a graph illustrating the change of blood IgE level involved in extrinsic atopic dermatitis, observed on day 1, day 7, and day 14 after the administration of the herb extract or the lactic acid bacteria fermented herb extract of the present invention to the test animal induced with atopic dermatitis. AD: induced with atopic dermatitis or not (+: induced with atopic dermatitis, −: not induced with atopic dermatitis), KIOM-MA: administered with the herb extract/fermented herb extract or not (+: administered, −: not administered), C: the herb extract of the present invention, 128: the fermented herb extract of the present invention, PC: positive control (Dexa.1; dexamethasone 1 mg/kg).

As a result, when the herb extract and the fermented herb extract of the present invention were administered, blood IgE level was decreased dose-dependently. In particular, blood IgE level was significantly decreased in the group administered with the fermented herb extract even after 14 days from the administration, compared with not only that in the negative control but also that in the positive control (p<0.01) (FIG. 4).

Manufacturing Example 1

Preparation of Pharmaceutical Formulations Containing the Herb Extract or the Fermented Herb Extract <1-1> Preparation of Syrups Syrups containing the herb extract or the fermented herb extract of the present invention by 2% (weight/volume) as an effective ingredient were prepared as follows. The herb extract or the fermented herb extract prepared in Example 1 or Example 2, saccharin and glucose were dissolved in 80 g of warm water. The mixture was cooled down, to which a mixture of glycerin, saccharin, flavors, ethanol, sorbic acid and distilled water was added. Water was added to the mixture, making a total volume of 100 ml (Table 3).

Composition of the syrup was as follows.

| Herb extract or fermented herb extract | 2 g |
|---|---|
| Saccharin | 0.8 g |
| Sucrose | 25.4 g |
| Glycerine | 8.0 g |
| Flavor | 0.04 g |
| Ethanol | 4.0 g |
| Sorbic acid | 0.4 g |
| Distiled water | proper amount |

2-2> Preparation of Tablets

Tablets containing 15 mg of the herb extract or the fermented herb extract of the present invention as an effective ingredient were prepared as follows.

250 g of the herb extract or the fermented herb extract prepared in Example 1 or Example 2, 175.9 g of lactose, 180 g of potato-starch and 32 g of colloidal silicic acid were all mixed together. 10% gelatin solution was added to the mixture, which was then pulverized and filtered with 14-mesh sieve. The pulverized mixture was dried, to which 160 g of potato-starch, 50 g of talc and 5 g of magnesium stearate were added to prepare tablets.

| Herb extract or fermented herb extract | 250 g |
|---|---|
| Lactose | 175.9 g |
| Potato-starch | 180 g |
| Colloidal silicic acid | 32 g |
| 10% gelatin solution | proper amount |
| Potato-starch | 160 g |
| Talc | 50 g |
| Magnesium stearate | 5 g |

Manufacturing Example 2

Preparation of Health Foods Containing the Herb Extract or the Fermented Herb Extract <2-1> Preparation of Foods Foods containing the herb extract or the fermented herb extract of the present invention prepared in Example 1 or Example 2 were prepared as follows.

1. Preparation of Spices for Cooking

Health enhancing spices for cooking were prepared with 20-95 weight % of the herb extract or the fermented herb extract of the present invention according to the conventional method.

2. Preparation of Tomato Ketchup and Sauce

Health enhancing tomato ketchup or sauce was prepared by mixing 0.2-1.0 weight % of the herb extract or the fermented herb extract of the present invention with tomato ketchup or sauce according to the conventional method.

3. Preparation of Flour Food 0.5-5.0 weight % of the herb extract or the fermented herb extract of the present invention was added to the flour. Health enhancing foods such as bread, cake, cookies, crackers and noodles were prepared with the flour mixture according to the conventional method.

4. Preparation of Soups and Gravies 0.1-5.0 weight % of the herb extract or the fermented herb extract of the present invention was added to soups and gravies. Health enhancing meat products, soups and gravies were prepared with this mixture by the conventional method.

5. Preparation of Ground Beef

Health enhancing ground beef was prepared by mixing 10 weight % of the herb extract or the fermented herb extract of the present invention with ground beef according to the conventional method.

6. Preparation of Dairy Products 5-10 weight % of the herb extract or the fermented herb extract of the present invention was added to milk. Health enhancing dairy products such as butter and ice cream were prepared with the milk mixture according to the conventional method.

7. Preparation of Sun-Sik

Brown rice, barley, glutinous rice and Yulmu (Job's tears) were gelatinized according to the conventional method, dried and pulverized to obtain 60-mesh powders. Black soybean, black sesame and wild sesame were steamed and dried according to the conventional method and pulverized to obtain 60-mesh powders. The herb extract or the fermented herb extract of the present invention was concentrated under reduced pressure, spray-dried and pulverized to obtain 60-mesh dry powders. Sun-Sik was prepared by mixing the dry powders of the grains, seeds and the herb extract or the fermented herb extract of the present invention according to the below ratio.

Grains (brown rice: 30 weight %, Yulmu: 15 weight %, barley: 20 weight %),

Seeds (wild sesame: 7 weight %, black soybean: 8 weight %, black sesame: 7 weight %), Dry powders of the herb extract or the fermented herb extract of the present invention (3 weight %),

*Ganoderma lucidum* (0.5 weight %),
*Rehmannia glutinosa* (0.5 weight %)

2-2> Preparation of Beverages

1. Preparation of Carbonated Beverages

Syrup was prepared by mixing the herb extract or the fermented herb extract of the present invention with sugar (5-10%), citric acid (0.05-0.3%), caramel (0.005-0.02%) and vitamin C (0.1-1%). The syrup was sterilized at 85-98° C. for 20-180 seconds, and then mixed with cooling water at the ratio of 1:4. Carbon dioxide was injected thereto by 0.5-0.82% to prepare carbonated beverages containing the herb extract or the fermented herb extract of the present invention.

2. Preparation of Health Beverages

The herb extract or the fermented herb extract of the present invention (0.5%) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

3. Preparation of Vegetable Juice

Health enhancing vegetable juice was prepared by adding 0.5 g of the herb extract or the fermented herb extract of the present invention to 1,000 ml of tomato or carrot juice according to the conventional method.

4. Preparation of Fruit Juice

Health enhancing fruit juice was prepared by adding 1 g of the herb extract or the fermented herb extract of the present invention to 1,000 ml of apple or grape juice according to the conventional method.

Manufacturing Example 3

Preparation of Cosmetics Containing the Herb Extract or the Fermented Herb Extract <3-1> Preparation of Emulsified Cosmetics Emulsified cosmetics were prepared according to the composition shown in Table 3. The method for the preparation is as follows.

1) heating the mixture comprising the raw materials 1-9 at 65-70° C.;

2) adding the raw material 10 to the mixture of step 1);

3) dissolving the mixture comprising the raw materials 11-13 by heating at 65-70° C.;

4) slowly adding the mixture of step 2) during performing step 3), followed by emulsification at 8,000 rpm for 2-3 minutes;

5) dissolving the raw material 14 in water and then adding the solution to the mixture of step 4), followed by emulsification for 2 minutes;

6) weighing the raw materials 15-17, which were added to the mixture of step 5), followed by emulsification for 30 seconds; and 7) degassing the mixture of step 6) finished with the emulsification process and then cooling thereof at 25-35° C. to give emulsified cosmetics.

TABLE 3

| Composition | Emulsified formulation 1 | Emulsified formulation 2 | Emulsified formulation 3 |
|---|---|---|---|
| 1 Stearic acid | 0.3 | 0.3 | 0.3 |
| 2 Stearyl alcohol | 0.2 | 0.2 | 0.2 |
| 3 Glyceryl monostearate | 1.2 | 1.2 | 1.2 |
| 4 Wax | 0.4 | 0.4 | 0.4 |
| 5 Polyoxyethylenesorbitan monolauric acid ester | 2.2 | 2.2 | 2.2 |
| 6 Paraoxybenzoic acid methyl | 0.1 | 0.1 | 0.1 |
| 7 Paraoxybenzoic acid propyl | 0.05 | 0.05 | 0.05 |
| 8 Cetyl ethyl hexanoate | 5 | 5 | 5 |
| 9 Triglyceride | 2 | 2 | 2 |
| 10 Cyclomethicone | 3 | 3 | 3 |

TABLE 3-continued

| Composition | Emulsified formulation 1 | Emulsified formulation 2 | Emulsified formulation 3 |
|---|---|---|---|
| 11 Distilled water | to 100 | to 100 | to 100 |
| 12 Concentrated Glycerin | 5 | 5 | 5 |
| 13 Triethanolamine | 0.15 | 0.15 | 0.15 |
| 14 Polyacrylic acid polymer | 0.12 | 0.12 | 0.12 |
| 15 Pigment | 0.0001 | 0.0001 | 0.0001 |
| 16 Flavor | 0.10 | 0.10 | 0.10 |
| 17 Herb extract or fermented herb extract | 0.0001 | 1 | 10 |

<3-2> Preparation of Solubilized Cosmetics

Solubilized cosmetics were prepared according to the composition shown in Table 4. The method for the preparation is as follows.

1) adding the raw materials 2-6 to the raw material 1 (purified water), which were dissolved by using Agi-mixer;
2) adding the raw materials 8-11 to the raw material 7 (alcohol) and completely dissolved; and
3) slowly adding the mixture of step 2) to the mixture of step 1), followed by solubilization.

TABLE 4

| Composition | Solubilized formulation 1 | Solubilized formulation 2 | Solubilized formulation 3 |
|---|---|---|---|
| 1 Purified water | to 100 | to 100 | to 100 |
| 2 Concentrated glycerin | 3 | 3 | 3 |
| 3 1,3-butyleneglycol | 2 | 2 | 2 |
| 4 EDTA-2Na | 0.01 | 0.01 | 0.01 |
| 5 Pigment | 0.0001 | 0.0002 | 0.0002 |
| 6 Herb extract or fermented herb extract | 0.1 | 5 | 5 |
| 7 Alcohol (95%) | 8 | 8 | 8 |
| 8 Paraoxybenzoic acid methyl | 0.1 | 0.1 | 0.1 |
| 9 Polyoxyethylene hydrogenated ester | 0.3 | 0.3 | 0.3 |
| 10 Flavor | 0.15 | 0.15 | 0.15 |
| 11 Cyclomethicone | — | — | 0.2 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A herb extract prepared by extracting a herb mixture consisting of *Sophora flavescens*, Licorice (*Glycyrrhiza uralensis*), *Lonicera jabonica*, *Angelica gigas*, *Aralia continentalis*, *Saussurea lappa*, *Bangpoong* (*Saposhnikovia divaricata*), *Zizyphus jujuba*, *Houttuynia cordata*, *Forsythia koreana*, *Arctii Fructus*, *Epimedium koreanum*, *Ginseng*, *Lithospermi Radix*, *Sanguisorbae officinalis*, *Cnidium officinale*, *Scrophularia buergeriana*, and *Reynoutria elliptica* by using water or an organic solvent.

2. The herb extract according to claim 1, wherein the herb extract is extracted by hot-water extraction from the herb mixture consisting of 10 weight parts of *Sophora flavescens*, 2-8 weight parts of Licorice (*Glycyrrhiza uralensis*), 2-8 weight parts of *Lonicera jabonica*, 2-8 weight parts of *Angelica gigas*, 2-8 weight parts of *Aralia continentalis*, 2-8 weight parts of *Saussurea lappa*, 2-8 weight parts of *Bangpoong* (*Saposhnikovia divaricata*), 2-8 weight parts of *Zizyphus jujuba*, 5-15 weight parts of *Houttuynia cordata*, 2-8 weight parts of *Forsythia koreana*, 5-15 weight parts of *Arctii Fructus*, 2-8 weight parts of *Epimedium koreanum*, 5-15 weight parts of *Ginseng*, 2-8 weight parts of *Lithospermi Radix*, 2-8 weight parts of *Sanguisorbae officinalis*, 2-8 weight parts of *Cnidium officinale*, 5-15 weight parts of *Scrophularia buergeriana*, and 2-8 weight parts of *Reynoutria elliptica*.

3. A fermented herb extract prepared by fermenting an herb extract by inoculating lactic acid bacteria thereto,
wherein the herb extract is prepared by extracting a herb mixture consisting of *Sophora flavescens*, Licorice (*Glycyrrhiza uralensis*), *Lonicera jabonica*, *Angelica gigas*, *Aralia continentalis*, *Saussurea lappa*, *Bangpoong* (*Saposhnikovia divaricata*), *Zizyphus jujuba*, *Houttuynia cordata*, *Forsythia koreana*, *Arctii Fructus*, *Epimedium koreanum*, *Ginseng*, *Lithospermi Radix*, *Sanguisorbae officinalis*, *Cnidium officinale*, *Scrophularia buergeriana*, and *Reynoutria elliptica* by using water.

4. The fermented herb extract according to claim 3, wherein the lactic acid bacteria is selected from the group consisting of *Lactobacillus* sp., *Bifidobacterium* sp., *Streptococcus* sp., *Leuconostoc* sp., *Pediococcus* sp., and *Lactococcus* sp.

5. The fermented herb extract according to claim 4, wherein the lactic acid bacteria is *Lactobacillus rhamnosus*.

6. The fermented herb extract according to claim 3, wherein the lactic acid bacteria is inoculated at the concentration of 0.5-5 weight % by the total weight of the sample.

7. The fermented herb extract according to claim 3, wherein the lactic acid bacteria is fermented at the temperature of 20-40° C. for 24-52 hours.

8. A pharmaceutical composition for the prevention or treatment of atopic dermatitis comprising the herb extract of claim 1 as an active ingredient.

9. A health food for the prevention or improvement of atopic dermatitis comprising the herb extract of claim 1 as an active ingredient.

10. A cosmetic composition for the prevention or improvement of atopic dermatitis comprising the herb extract of claim 1 as an active ingredient.

11. A pharmaceutical composition for the prevention or treatment of atopic dermatitis comprising the fermented herb extract of claim 3 as an active ingredient.

12. A health food for the prevention or improvement of atopic dermatitis comprising the fermented herb extract of claim 3 as an active ingredient.

13. A cosmetic composition for the prevention or improvement of atopic dermatitis comprising the fermented herb extract of claim 3 as an active ingredient.

* * * * *